United States Patent
Leitner et al.

(10) Patent No.: US 6,388,141 B1
(45) Date of Patent: May 14, 2002

(54) HYDROFORMYLATION WITH UNMODIFIED RHODIUM CATALYSTS IN SUPERCRITICAL CARBON DIOXIDE

(75) Inventors: Walter Leitner, Mülheim an der Ruhr; Daniel Koch, Duisburg, both of (DE)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 0 days.

(21) Appl. No.: 09/462,855

(22) PCT Filed: Jul. 11, 1998

(86) PCT No.: PCT/EP98/04319

§ 371 Date: Jan. 13, 2000

§ 102(e) Date: Jan. 13, 2000

(87) PCT Pub. No.: WO99/03810

PCT Pub. Date: Jan. 28, 1999

(30) Foreign Application Priority Data

Jul. 18, 1997 (DE) .......................... 197 30 783

(51) Int. Cl.$^7$ .......................... C07C 45/50; C07C 51/10
(52) U.S. Cl. .................. 568/451; 568/429; 568/447; 568/454; 568/378; 562/406; 562/522
(58) Field of Search ............... 568/429, 447, 568/489, 451, 454, 909, 378; 562/406, 522

(56) References Cited

U.S. PATENT DOCUMENTS

| | | | |
|---|---|---|---|
| 4,124,619 A | 11/1978 | Fitton et al. | 260/410.6 |
| 4,568,653 A | 2/1986 | Schwirten et al. | 502/34 |
| 5,198,589 A | 3/1993 | Rathke et al. | 568/454 |

OTHER PUBLICATIONS

Patent Abstracts of Japan vol. 014, No. 134 (C–0701), 14. Marz 1990 & JP 02 006424 A (Nippon Petrochem Co. Ltd), 10. Januar 1990 siehe Zusammenfassung.

Kainz, et al., "Iridium–Catalyzed Enantioselective Hydrogenation of Imines in Supercritical Carbon Dioxide"; 10. 1021/ja984309i CCC:$18.00, © xxxx American Chemical Society (1998).

*Primary Examiner*—Sreeni Padmanabhan
(74) *Attorney, Agent, or Firm*—Norris McLaughlin & Marcus

(57) ABSTRACT

The present invention relates to processes for the preparation of oxo products by the hydroformylation of substrates having C═C double bonds using unmodified rhodium catalysts in a reaction mixture essentially consisting of the substrates, the catalyst and carbon dioxide in a supercritical state ($scCO_2$). In particular, the invention relates to such processes for the preparation of products which contain substantial proportions of branched i-oxo products. Further, the invention relates to such processes for the hydroformylation of substrates which do not correspond to the general formula $C_nH_{2n}$. The invention further relates to such processes in which the separation of product and catalyst is effected using the special solvent properties of $scCO_2$.

21 Claims, No Drawings

HYDROFORMYLATION WITH UNMODIFIED RHODIUM CATALYSTS IN SUPERCRITICAL CARBON DIOXIDE

This application is a 371 of PCT/EP98/04319, which was filed on Jul. 11, 1998.

The present invention relates to processes for the preparation of oxo products by the hydroformylation of substrates having C=C double bonds using unmodified rhodium catalysts in a reaction mixture essentially consisting of the substrates, the catalyst and carbon dioxide in a supercritical state ($scCO_2$). In particular, the invention relates to such processes for the preparation of products which contain substantial proportions of branched i-oxo products. Further, the invention relates to such processes for the hydroformylation of substrates which do not correspond to the general formula $C_nH_{2n}$. The invention further relates to such processes in which the separation of product and catalyst is effected using the special solvent properties of $scCO_2$.

The transition metal catalyzed reaction of substrates containing C=C double bonds with a mixture of hydrogen ($H_2$) and carbon monoxide (CO) is referred to as hydroformylation or oxo reaction; it is a technically important method for the preparation of aldehydes and alcohols (oxo products). More than 6 million tons per year of oxo products are produced by catalytic hydroformylation worldwide. These products are employed as plasticizers and modifiers for PVC and other polymers, in detergent production, and as fine chemicals and as intermediates for the production of agrochemicals, food additives and pharmaceuticals (C. D. Frohning, C. W. Kohlpaintner, in Applied Homogeneous Catalysis with Organometallic Compounds (editors: B. Cornils, W. A. Herrmann), VCH, Weinheim, 1996, Vol. 1, Section 2.1.1).

Depending on the reaction parameters, the catalysts and the substitution pattern at the C=C double bond of the substrate, linear (normal, n-) or branched (iso, i-) oxo products are produced more or less selectively in the hydroformylation. Of the oxo products of simple short-chain olefins of general formula $C_nH_{2n}$ (n=2, 3), it is mainly the n-products which are economically important. Of the long-chain olefins $C_nH_{2n}$ (n≧4), the branched i-oxo products are also economically important and are discussed, for example, as starting materials for the preparation of plasticizers in pure form or as mixtures with the n-oxo products. Above all, the i-oxo products are also particularly important for substrates with functionalized C=C double bonds, i.e., substrates which do not correspond to the general formula $C_nH_{2n}$. In particular, reference may be made herein to the technical synthesis of vitamin A described in U.S. Pat. No. 3,840,589, DE 2 03 078 and U.S. Pat. No. 4,124,619, which involves the formation of an i-aldehyde by the hydroformylation of substrates comprising allyl ester moieties. The formation of branched products in the hydroformylation of vinyl aromatics (e.g., styrene) is discussed as a possible route to α-aryl-carboxylic acids, which are employed, inter alia, as analgetics and antirheumatics (e.g., Ibuprofen®, Naproxen®, Suprofen®).

The catalysts for hydroformylation can be classified into so-called "unmodified" and "modified" catalysts which are respectively preferred for particular processes or particular substrates according to the prior art (C. D. Frohning, C. W. Kohlpaintner, supra, p. 33ff). "Modified" systems means catalysts in which the catalytically active metal component contains additional ligands, usually phosphorus compounds, in addition to H and CO for increasing the useful life and for controlling activity or selectivity. The term "unmodified catalysts" denotes all other metal compounds which are capable of forming catalytically active hydrido-carbonyl compounds under the reaction conditions. Technical importance has been achieved to date mainly by catalysts based on the metals cobalt (Co) and rhodium (Rh). The separation of the products and recovery of the catalysts is an important factor in the technical realization of hydroformylation reactions.

Supercritical ("fluid") carbon dioxide ($scCO_2$), i.e., compressed carbon dioxide at temperatures and pressures beyond the critical point ($T_c$=31.0° C., $p_c$=73.75 atm, $d_c$=0.467 g·ml$^{-1}$) is employed as a reaction medium for hydroformylation in U.S. Pat. No. 5,198,589 and in German Application DE-A-197 02 025.9 (Jan. 23, 1997). Carbon dioxide in a supercritical state is an interesting solvent for performing catalytic reactions because it is toxicologically and ecologically safe, in contrast to conventional organic solvents. Further, $scCO_2$ has the property of being completely miscible with many gaseous reaction partners within wide limits, whereby limitation of the reaction rate by diffusion processes, which frequently occurs in gas/liquid phase reactions, is totally avoided. Further, due to the solvent properties of $scCO_2$ which vary as a function of pressure and temperature, separation of main or side products from the reaction mixture is possible in favorable cases when the external parameters are appropriately selected. A survey of catalytic reactions in $scCO_2$ is found in Science 1995, 269, 1065.

In DE-A-197 02 025.9, modified rhodium catalysts are employed for the hydroformylation in $scCO_2$, specially developed phosphorus compounds ensuring high solubility of the catalysts in $scCO_2$. Thus, the stated advantageous properties of $scCO_2$ can be fully utilized with modified rhodium catalysts, but the preparation of the phosphorus ligands is an additional cost factor in possible technical applications. In U.S. Pat. No. 5,198,589, unmodified cobalt catalysts are employed for the hydroformylation of simple olefins $C_nH_{2n}$ in $scCO_2$. As compared to conventional solvents, similar reaction rates are obtained with significantly higher selectivities in favor of the linear n-oxo products. This increase in selectivity in favor of the n-oxo products is attributed to the use of $scCO_2$ as the reaction medium.

We have now found that unmodified rhodium catalysts can be efficiently used for hydroformylation in $scCO_2$ to obtain, surprisingly, not only significantly higher reaction rates, but also significantly higher selectivities in favor of the branched i-oxo products than are obtained in conventional solvents.

Rhodium catalyzed hydroformylations in $scCO_2$ are conveniently performed by charging the catalyst or catalyst precursor and the substrate into a high-pressure reactor and then pressurizing with $H_2$ and CO, either as a mixture or successively, at room temperature up to the desired partial pressure. Then, the amount of $CO_2$ required to reach the desired density of the reaction medium is filled into the reactor. Then, heating to the desired reaction temperature is performed with stirring. After said temperature has been reached, the stirrer can be turned off due to the fast diffusion within the homogeneous supercritical phase. After the desired reaction time, the pressure is released from the reactor, during which the products can be isolated from the supercritical phase using appropriate known methods (K. Zosel, Angew. Chem. 1978, 90, 748; M. A. McHugh, V. J. Krukonis, Supercritical Fluid Extraction: Principle and Practice, Butterworths, Stoneham, 1994). Due to the fact that the solubilities of the metal species and the products are clearly different, the catalysts can be easily separated from the products and recycled.

As catalysts or catalyst precursors for the formation of unmodified Rh systems in scCO$_2$, salts, complexes or cluster compounds of rhodium in any oxidation state can be employed. Compounds 1–8 are preferred examples of such catalysts or catalyst precursors, without intending to limit the choice of the catalyst to the structures shown. Particularly preferred catalysts are complex compounds of rhodium, 4–8, containing carbonyl ligands (CO) or ligands which can be readily replaced by CO under the reaction conditions. The amount of catalyst can be freely selected within a broad range depending on the reaction conditions and the reactivity of the substrates. Typical amounts of catalysts, based on the amount of substrate employed, range from 0.001 to 10 mole percent, preferably from 0.01 to 1 mole percent, more preferably from 0.05 to 0.5 mole percent.

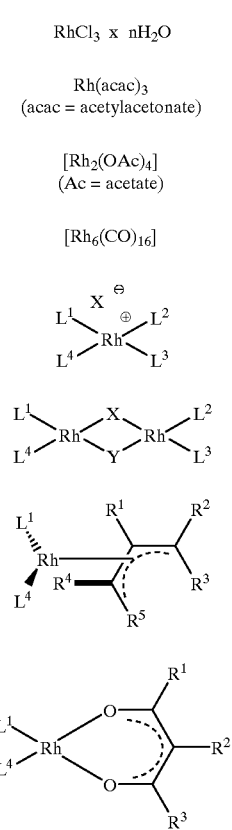

$R^1$–$R^5$ are residues independently selected from hydrogen, $C_1$–$C_{20}$ alkyl, $C_2$–$C_{20}$ alkenyl, $C_2$–$C_{20}$ alkynyl, aryl, $C_1$–$C_{20}$ perfluoroalkyl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, arylthio, $C_1$–$C_{20}$ alkylsilyl, arylsilyl, $C_1$–$C_{20}$ alkyloxysilyl or aryloxysilyl, each of which may optionally be substituted with $C_1$–$C_{12}$ alkyl, $C_1$–$C_{12}$ perfluoroalkyl, halo, $C_1$–$C_5$ alkoxy, $C_1$–$C_{12}$ carboxylate, $C_2$–$C_{12}$ alkoxycarbonyl or aryl. Residues $R^1$–$R^5$ may be connected with one another in cyclic compounds.

$L^1$–$L^4$ are neutral ligands independently selected from the group consisting of CO, $R^1R^2C$=$CR^3R^4$, $R^1C$≡$CR^2$, $NR^1R^2R^3$, wherein $R^1$–$R^4$ are as defined above. $L^1$–$L^4$ may be connected with one another in cyclic compounds.

X, Y are anions or ligands with one negative charge, independently selected from the group consisting of $R^-$, $F^-$, $Cl^-$, $Br^-$, $I^-$, $RO^-$, $RCO_2^-$, $p$-$C_6H_4SO_3^-$, $PF_6^-$, $BF_4^-$, $BR_4^-$, wherein R is defined as mentioned for $R^1$–$R^5$.

Possible substrates for the rhodium catalyzed hydroformylation in scCO$_2$ are compounds containing at least one C=C double bond which, on one hand, allow a hydroformylation reaction due to their substitution pattern, and on the other hand, are sufficiently soluble in scCO$_2$ so that homogeneous solutions are obtained during the reaction. Preferred are substrates with a C=C double bond as represented by general formula 9. Mixtures of such compounds may also be used as substrates. The amount of substrate employed is not critical as long as complete solubility in the supercritical medium is achieved. Based on the reactor volume, typical substrate quantities are 0.05–5 mol/l, preferably 0.1–2 mol/l.

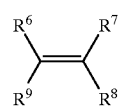

9

$R^6$–$R^9$ are residues independently selected from hydrogen, $C_1$–$C_{20}$ alkyl, $C_2$–$C_{20}$ alkenyl, $C_2$–$C_{20}$ alkynyl, aryl, $C_1$–$C_{20}$ perfluoroalkyl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, arylthio, $C_1$–$C_{20}$ alkylsilyl, arylsilyl, $C_1$–$C_{20}$ alkyloxysilyl, aryloxysilyl, $C_1$–$C_{20}$ alkylsilyloxy, $C_1$–$C_{20}$ alkyloxysilyloxy, $C_1$–$C_{20}$ alkylsulfonyl, $C_1$–$C_{20}$ alkylsulfinyl or halo, each of which may optionally be substituted with additional residues corresponding to the same definition as $R^6$–$R^9$. Residues $R^6$–$R^9$ may be connected with one another in cyclic compounds.

The partial pressure of H$_2$ and CO can be widely varied. Typical pressures at room temperature are between 0.1 bar and 100 bar for each of H$_2$ and CO, preferably between 1 bar and 30 bar. The influence of the H$_2$ and CO partial pressure on the reaction rate and selectivity is largely identical with the trends found in conventional solvents (C. D. Frohning, C. W. Kohlpaintner, supra, p. 55ff). Much the same applies to the reaction temperature the lower limit of which is determined by the critical temperature of CO$_2$ (T$_c$=31° C.). Typical reaction temperatures for hydroformylation with unmodified rhodium catalysts in scCO$_2$ are between 31° C. and 150° C., preferably between 35° C. and 100° C. When the H$_2$/CO pressure and the reactor volume are given, the total pressure prevailing at the reaction temperature is determined by the amount of CO$_2$. The minimum amount thereof is determined by the critical density of CO$_2$ (d$_c$=0,467 g·ml$^{-1}$), while the upper limit depends on the maximum admissible system test pressure of the reactors employed. For standard V$_2$A high pressure reactors with inspection glasses, this results in a typical range for the amount of CO$_2$ employed, based on the reactor volume, of from 0.46 g·ml$^{-1}$ to 0.90 g·ml$^{-1}$, preferably from 0.5 g·ml$^{-1}$ to 0.75 g·ml$^{-1}$.

Reactions according to the present invention may also be performed in the presence of one or more additives to provide, for example, an easier handling of the substrates or catalysts, or an improvement of the solvent properties of the reaction medium, or an increase of the reaction rate, or an improvement of the yield. Such additives may be independently selected, for example, from water, amines, perfluorinated compounds, organic solvents (e.g., dichloromethane, trichloromethane, tetrachloromethane, 1,2-dichloroethane, trichloroethene, benzene, toluene, xylene, cumene, hexane, cyclohexane, halobenzenes, tetrahydrofuran, tert-butyl methyl ether, diethyl ether, dimethoxyethane, dimethylformamide, ethyl acetoacetate, acetone, dimethyl carbonate, alcohols).

In order to ensure that the reaction will start only after the supercritical state is reached, it may be convenient, depending on the reactivity of the substrate, to supply the catalyst and the substrate in a spatially separated way. Thus, for example, either the substrate or the catalyst may be supplied to the reactor in a separate storage vessel open at the top. One component may also be supplied in a second pressure vessel which is connected with the reactor through a valve. It is also possible to supply the catalyst in glas ampoules which can be cracked under the reaction conditions. Another alternative is the continuous or discontinuous metering of a component by means of a pump system.

Example 1 describes the typical procedure adopted in the hydroformylation in $scCO_2$ with unmodified rhodium catalysts and illustrates the increased reaction rate and the unexpected change of selectivity when $scCO_2$ is used as compared to a conventional solvent. The Examples summarized in Table 1 describe the hydroformylation of some prototypical compounds in $scCO_2$ under typical conditions, but are not intended to limit the scope, the application range or the advantages of the present invention in any way.

EXAMPLE 1

Comparison between the hydroformylations in $scCO_2$ and in toluene of 1-octene and trans-3-hexene with [(cod)Rh(hfacac)] (cod=1,5-cyclooctadiene, hfacac=hexafluoroacetylacetonate) as a catalyst In a pressure reactor (V=25 ml) flushed with argon, 2.9 mg of [(cod)Rh(hfacac)] ($6.9 \times 10^{-1}$ mmol) and 508 mg of 3-hexene (6.04 mmol) were provided in a spatially separated way. Then, the reactor was pressurized with a 1:1 gas mixture of $CO/H_2$ at room temperature to a pressure of 45 bar. Subsequently, 13.5 g of $CO_2$ was filled in the pressure reactor using a compressor and heated to 45° C. to provide an internal pressure of about 160 bar. After 20 h, the pressure was released from the reactor through a cooling trap cooled to −50° C. with dry ice/acetone. A $^1H$ NMR spectroscopical analysis of the components trapped in the cooling trap showed a quantitative conversion of 3-hexene and a composition of the oxo products of 86% 2-ethylpentanal and 14% 2-methylhexanal.

In a comparative experiment, 2.7 mg of [(cod)Rh(hfacac)] ($6.4 \times 10^{-1}$ mmol) and 508 mg of trans-3-hexene (6.04 mmol) were provided in 25 ml of toluene in a pressure reactor (V=50 ml) flushed with argon. Then, the reactor was pressurized with a 1:1 gas mixture of $CO/H_2$ at room temperature to a pressure of 45 bar, followed by heating to 45° C. The reaction mixture was stirred for 20 h and then, after cooling, the residual gas was released. A $^1H$ NMR spectroscopical analysis of the toluene solution showed a conversion of 3-hexene of only 23%, mainly to form 2-ethylpentanal.

In an analogous way, two experiments were performed with 1-octene as the substrate. In $scCO_2$, a quantitative conversion of 1-octene was achieved after 20 h at 40° C. as shown by NMR analysis. The composition of the oxo products was 58% n-nonanal and 42% i-aldehydes (2-methyloctanal, 2-ethylheptanal and other internal aldehydes). In toluene, the conversion was only 61%, conditions being otherwise identical, and the oxo products consisted of 63% n-nonanal and 37% 2-methyloctanal.

TABLE 1

Rhodium catalyzed hydroformylation in $scCO_2$ [a]

| | catalyst | substrate | conditions | yield of oxo products [b] |
|---|---|---|---|---|
| Example 2 | [(cod)Rh(hfacac)] [c]<br>3.1 mg,<br>$7.4 \times 10^{-3}$ mmol (Rh) | 1-octene<br>540 mg, 4.81 mmol | $CO_2$: 0.52 g.ml$^{-1}$ [d]<br>$H_2/CO$ (1:1): 45 bar [e]<br>T = 60° C., t = 20 h | total: 97% (GC)<br>56% n-nonanal<br>44% i-aldehydes [f] |
| Example 3 | [(cod)Rh(hfacac)] [c]<br>2.8 mg,<br>$6.7 \times 10^{-3}$ mmol (Rh) | 1-octene<br>540 mg, 4.81 mmol | $CO_2$: 0.57 g.ml$^{-1}$ [d]<br>$H_2/CO$ (1:1): 30 bar [e]<br>T = 60° C., t = 20 h | total: 96% (GC)<br>53% n-nonanal<br>47% i-aldehydes [f] |
| Example 4 | [(cod)Rh(hfacac)] [c]<br>2.8 mg,<br>$6.7 \times 10^{-3}$ mmol (Rh) | 1-octene<br>540 mg, 4.81 mmol | $CO_2$: 0.53 g.ml$^{-1}$ [d]<br>$H_2/CO$ (1:1): 45 bar [e]<br>T = 80° C., t = 20 h | total: 91% (GC)<br>52% n-nonanal<br>48% i-aldehydes [f] |
| Example 5 | $RH_6(CO)^{16}$<br>6.3 mg,<br>$35.5 \times 10^{-3}$ mmol (Rh) | 1-octene<br>540 mg, 4.81 mmol | $CO_2$: 0.52 g.ml$^{-1}$ [d]<br>$H_2/CO$ (1:1): 45 bar [e]<br>T = 60° C., t = 20 h | total: >97% (NMR)<br>63% n-nonanal<br>37% i-aldehydes [f] |
| Example 6 | [(cod)Rh(hfacac)] [c]<br>2.9 mg,<br>$6.0 \times 10^{-3}$ mmol (Rh) | 3-hexene<br>508 mg, 6.04 mmol | $CO_2$: 0.54 g.ml$^{-1}$ [d]<br>$H_2/CO$ (1:1): 45 bar [e]<br>T = 60° C., t = 24 h | total: >97% (NMR)<br>86% 2-ethylpentanal<br>14% 2-methylhexanal |
| Example 7 | [(cod)Rh(hfacac)] [c]<br>2.4 mg,<br>$5.7 \times 10^{-3}$ mmol (Rh) | styrene<br>410 mg, 3.94 mmol | $CO_2$: 0.51 g.ml$^{-1}$ [d]<br>$H_2/CO$ (1:1): 45 bar [e]<br>T = 60° C., t = 20 h | total: >97% (NMR)<br>15% 3-phenylpropanal<br>85% 2-phenylpropanal |
| Example 8 | [(cod)Rh(hfacac)] [c]<br>2.5 mg,<br>$6.0 \times 10^{-3}$ mmol (Rh) | ethyl acrylate<br>480 mg, 4.80 mmol | $CO_2$: 0.52 g.ml$^{-1}$ [d]<br>$H_2/CO$ (1:1): 45 bar [e]<br>T = 60° C., t = 20 h | total: 18% (NMR)<br>14% ethyl 4-oxobutyrate<br>86% ethyl 2-methyl-3-oxopropionate |
| Example 9 | [(cod)Rh(hfacac)] [c]<br>2.5 mg,<br>$6.0 \times 10^{-3}$ mmol (Rh) | allyl acetate<br>465 mg, 4.66 mmol | $CO_2$: g.ml$^{-1}$ 0.58 [d]<br>$H_2/CO$ (1:1): 45 bar [e]<br>T = 60° C., t = 20 h | total: >97% (NMR)<br>28% 4-oxobutylacetate<br>72% 3-oxo-2-methylpropyl acetate |

TABLE 1-continued

Rhodium catalyzed hydroformylation in scCO₂ [a]

| catalyst | substrate | conditions | yield of oxo products [b] |

[a] All experiments were performed in a stainless steel high-pressure reactor equipped with an inspection glass. In all cases, the reaction mixtures were homogeneous and yellow in color during the reaction.
[b] In all cases, the product ratios were determined using the intensities from the aldehyde protons in a $^1$H NMR spectrum.
[c] cod = 1,5-cyclooctadiene; hfacac = hexafluoroacetylacetonate.
[d] based on the reactor volume V = 25 ml.
[e] at room temperature.
[f] mixture of 2-methyloctanal, 3-ethylheptanal and other internal aldehydes.

What is claimed is:

1. A process for preparing a product comprising at least a substantial proportion of one or more branched i-oxo products by hydroformylating one or more substrates having at least one C═C double bond and not corresponding to the general formula $C_nH_{2n}$, said process comprising hydroformylating the one or more substrates when present in a reaction mixture consisting essentially of the one or more substrates, at least one unmodified rhodium catalyst and carbon dioxide in a supercritical state ($scCO_2$) to produce said product comprising said at least a substantial proportion of said one or more branched i-oxo products.

2. The process according to claim 1, wherein the unmodified rhodium catalyst or a precursor thereof is present in the reaction mixture in a concentration of from 0.001 to 10 mole percent based on the substrate, and said catalyst or precursor thereof is a salt, complex or cluster compound of rhodium in any oxidation state.

3. The process according to claim 2, wherein the unmodified rhodium catalyst or a precursor thereof is present in the reaction mixture in a concentration of from 0.01 to 1 mole percent based on the substrate, or said catalyst or precursor thereof has one of formulae 1–8:

$$RhCl_3 \times nH_2O \qquad 1$$

$$Rh(acac)_3 \qquad 2$$
(acac = acetylacetonate)

$$[Rh_2(OAc)_4] \qquad 3$$
(Ac = acetate)

$$[Rh_6(CO)_{16}] \qquad 4$$

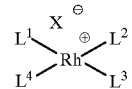

5

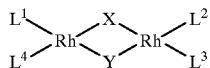

6

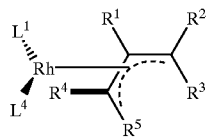

7

-continued

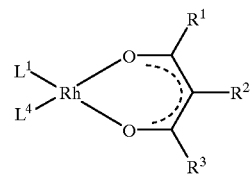

8 wherein $R^1$–$R^5$ are residues independently selected from hydrogen, $C_1$–$C_{20}$ alkyl, $C_2$–$C_{20}$ alkenyl, $C_2$–$C_{20}$ alkynyl, aryl, $C_1$–$C_{20}$ perfluoroalkyl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, arylthio, $C_1$–$C_{20}$ alkylsilyl, arylsilyl, $C_1$–$C_{20}$ alkyloxysilyl or aryloxysilyl, each of which may optionally be substituted with $C_1$–$C_{12}$ alkyl, $C_1$–$C_{12}$ perfluoroalkyl, halo, $C_1$–$C_5$ alkoxy, $C_1$–$C_{12}$ carboxylate, $C_2$–$C_{12}$ alkoxycarbonyl or aryl, and residues $R^1$–$R^5$ may also be connected with one another in cyclic compounds;

$L^1$–$L^4$ are neutral ligands independently selected from the group consisting of CO, $R^1R^2C$═$CR^3R^4$, $R^1C$≡$CR^2$, $NR^1R^2R^3$, wherein $R^1$–$R^4$ are as defined above, and $L^1$–$L^4$ may be connected with one another in cyclic compounds;

X, Y are anions or ligands with one negative charge, independently selected from the group consisting of $R^-$, $F^-$, $Cl^-$, $Br^-$, $I^-$, $RO^-$, $RCO_2^-$, $p\text{-}C_6H_4SO_3^-$, $PF_6^-$, $BF_4^-$, $BR_4^-$, wherein R is defined as mentioned for $R^1$–$R^5$.

4. The process according to claim 3, wherein the unmodified rhodium catalyst or a precursor thereof is present in the reaction mixture in a concentration of from 0.05 to 0.5 mole percent based on the substrate, or said catalyst or precursor thereof has one of formulae 4–8.

5. The process according to claim 1, wherein said one or more substrates are present in a concentration, based on the volume of a reactor containing the reaction mixture, of 0.05 to 5 mol/l, and are compounds or mixtures of compounds containing at least one double bond of the formula 9:

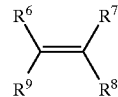

9 wherein residues $R^6$–$R^9$ may be any group provided a hydroformylation of the one or more substrates is possible, and it is possible to form homogeneous solutions of the one or more substrates in $scCO_2$.

6. The process according to claim 5, wherein said one or more substrates are present in a concentration, based on the volume of a reactor containing the reaction mixture, of 0.1 to 2 mol/l, or in the compounds of formula 9 residues $R^6$–$R^9$ are independently selected from hydrogen, $C_1$–$C_{20}$ alkyl, $C_2$–$C_{20}$ alkenyl, $C_2$–$C_{20}$ alkynyl, aryl, $C_1$–$C_{20}$perfluoroalkyl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, arylthio, $C_1$–$C_{20}$ alkylsilyl, arylsilyl, $C_1$–$C_{20}$ alkyloxysilyl, aryloxysilyl, $C_1$–$C_{20}$ alkylsilyloxy, $C_1$–$C_{20}$ alkyloxysilyloxy, $C_1$–$C_{20}$ alkylsulfonyl, $C_1$–$C_{20}$ alkylsulfinyl or halo, each of which may optionally be substituted with additional residues corresponding to the same definition as $R^6$–$R^9$, and residues $R^6$–$R^9$ may be connected with one another in cyclic compounds.

7. The process according to claim 1, wherein the partial pressures of reactant gases $H_2$ and CO are between 0.1 bar and 100 bar.

8. The process according to claim 7, wherein the partial pressures of reactant gases $H_2$ and CO are between 1 bar and 30 bar.

9. The process according to claim 1, which is conducted at a reaction temperature between 31° C. and 150° C.

10. The process according to claim 9, which is conducted at a reaction temperature between 35° C. and 100° C.

11. The process according to claim 1, wherein the amount of $CO_2$ employed, based on the volume of a reactor containing the reaction mixture, is within a range of from 0.46 g·ml$^{-1}$ to 0.90 g·ml$^{-1}$.

12. The process according to claim 11, wherein the amount of $CO_2$ employed, based on the volume of a reactor containing the reaction mixture, is within a range of from 0.5 g·ml$^{-1}$ to 0.75 g·ml$^{-1}$.

13. The process according to claim 1, wherein the reaction mixture contains one or more additional additives.

14. The process according to claim 13, wherein said one or more additional additives are selected from the group consisting of water, amines, perfluorinated compounds and organic solvents.

15. The process according to claim 14, wherein said organic solvents are selected from the group consisting of dichloromethane, trichloromethane, tetrachloromethane, 1,2-dichloroethane, trichloroethene, benzene, toluene, xylene, cumene, hexane, cyclohexane, halobenzenes, tetrahydrofuran, tert-butyl methyl ether, diethyl ether, dimethoxyethane, dimethylformamide, ethyl acetoacetate, acetone, dimethyl carbonate, and alcohols.

16. The process according to claim 1, wherein the one or more substrates and the catalyst are supplied to the reaction mixture in a spatially separated way before a supercritical state is reached.

17. The process according to claim 1, which further comprises separating said one or more i-oxo products from the catalyst by extraction with supercritical $CO_2$.

18. The process according to claim 17, which further comprises recovering the catalyst in an active form.

19. The process according to claim 1, which is for the preparation of one or more i-oxo products having 5 to 20 carbon atoms.

20. A process for preparing vitamin A, said process comprising the following steps:
   a) hydroformylating one or more substrates containing allyl ester moieties according to the process of claim 1; and
   b) converting the product of step a) to vitamin A.

21. A process for preparing an α-arylcarboxylic acid, said process comprising the following steps:
   a) hydroformylating one or more vinyl aromatic substrates according to the process of claim 1; and
   b) converting the product of step a) to said α-arylcarboxylic acids.

* * * * *